United States Patent [19]

Dawes

[11] 4,258,215

[45] Mar. 24, 1981

[54] HYDROFORMYLATION PROCESS

[75] Inventor: John L. Dawes, Longview, Tex.

[73] Assignee: Eastman Kodak Company, Rochester, N.Y.

[21] Appl. No.: 70,587

[22] Filed: Aug. 29, 1979

[51] Int. Cl.$^3$ .............................................. C07C 45/50
[52] U.S. Cl. .................................... 568/454; 568/451
[58] Field of Search ................. 260/604 HF; 568/909, 568/883, 428, 429, 451, 454

[56] References Cited

U.S. PATENT DOCUMENTS

| | | | |
|---|---|---|---|
| 3,527,809 | 9/1970 | Pruett et al. | 260/604 HF |
| 3,544,635 | 12/1970 | Kehoe et al. | 260/604 HF |
| 3,555,098 | 1/1971 | Olivier et al. | 260/604 HF |
| 3,557,219 | 1/1971 | Kehoe et al. | 260/604 HF |
| 3,733,362 | 5/1973 | Biale | 260/604 HF |
| 4,048,233 | 9/1977 | Falbe et al. | 260/604 HF |
| 4,159,999 | 7/1979 | Stauzzenberger et al. | 260/604 HF |

OTHER PUBLICATIONS

Hagihara et al., "Handbook of Organometallic Compounds", p. 918.

*Primary Examiner*—Werren B. Lone
*Attorney, Agent, or Firm*—Daniel B. Reece, III; J. Frederick Thomsen

[57] ABSTRACT

An improved method for the preparation of aldehydes by the hydroformylation of an alpha-olefin, carbon monoxide and hydrogen in the presence of a rhodium complex catalyst at a pressure of about 1,000 psig and in the presence of from about 1% to about 10% of water.

16 Claims, No Drawings

HYDROFORMYLATION PROCESS

This invention describes an improved method for the preparation of aldehydes by the hydroformylation of alpha-olefins in the presence of a suitable catalyst. More particularly this invention report describes an improved method for the hydroformylation of alpha-olefins in the presence of water and a rhodium complex catalyst at high pressure.

known methods for preparing aldehydes by the hydroformylation process involve slurry and homogeneous systems catalyzed by cobalt metal derivatives. U.S. Pat. No. 3,527,809 describes another hydroformylation process wherein hydrocarbonyl tris(triphenylphosphine) rhodium with added triphenylphosphine is used as a catalyst.

The present invention utilizes the catalyst described in U.S. Pat. No. 3,527,809 in an improved process. In this improved process the reactor is fed a two-phase mixture of water and catalyst-containing organics. Other known oxo processes use a single liquid phase. It is quite unexpected that rhodium carbonyl complexes would be stable at reaction conditions in the presence of water. It is known that many low valent rhodium carbonyl complexes react with water. For example, tetrarhodium dodecacarbonyl spontaneously decomposes in water (*Handbook of Organometallic Compounds* by Hagihara, Kumada, and Okaware, page 918).

In the process of the instant invention a mixture of alpha-olefin (for example, propylene), hydrogen, carbon monoxide, catalyst and water is introduced into a hydroformylation reactor. The water content fed to the reactor is held between 0.1 and 10.0 percent, the preferred operating range being from about 3 to about 5%. Reactor pressure is held at about 500 psig to about 3,000 psig, preferably about 500 psig to about 1,500 psig. A most preferred operating pressure is about 1,000 psig. A preferred catalyst is hydrocarbonyl tris(triphenylphosphine) rhodium with added triphenylphosphine as described in U.S. Pat. No. 3,527,809. Rhodium content in the reactor is maintained at from about 10 to about 1,000 parts per million (ppm), preferably about 10 ppm to about 100 ppm. A most preferred operating level is about 50 ppm. The reaction may be conducted in a medium containing as low as 5 ppm rhodium or a 100% catalyst solution. Economic factors relating to rhodium metal dictate a practical catalyst level which has been found to be approximately 50 ppm. The reaction is conducted at temperatures of from about 90° C. to about 160° C. with a preferred operating range being from about 100° C. to 140° C. The temperature should not be permitted to exceed 160° C. as catalyst decomposition will commence at that point. The effluent from the reactor is cooled and passed through conventional successive high and low pressure separators to recover the unreacted gases. The liquid material from the final separator is introduced into an azeotropic distillation column operated at a base temperature of from about 60° to about 100° C., preferrably about 75° C. The overhead from this distillation column is separated in a decanter. The product aldehydes are recovered as the organic layer from the decanter. The water layer may be recycled to the distillation column. This reflux reduces the column temperature and inhibits high boiler formation. The base stream from the distillation column contains water, organic high boilers such as glycols, acids, etc., some aldehydes and the catalyst. This base stream is introduced into a separator where the water is separated for recycle to the reactor. The organic stream from the separator is fed to a gas stripping column. Hot gas, such as nitrogen, propylene, synthesis gas or recycled reactor gas is introduced into the stripping column so that the aldehydes, high boilers and butyric acid are removed from the top of the column. Temperature in the column is maintained below 160° C., the decomposition point of the catalyst. Preferably the column will be operated at a temperature of 110° C. or less. The catalyst mixture withdrawn from the base of the gas stripper is adjusted with aldehydes to the desired rhodium concentration and recycled to the reactor. This improved process gives increased rates, conversions and yields, eliminates the need for any additional solvent as a catalyst carrier, reduces high boiler formation and regenerates the catalyst for reintroduction into the reactor.

Surprisingly, it has been found that the gas stripping is the only method that successfully removes the poisons from the catalyst of the instant invention. Water and caustic washes were unsuccessful in restoring catalyst activity. Caustic washings also caused further formation of high boiling condensation products.

It is also quite unexpected that the introduction of water into the system would produce significant advantages. The presence of two phases entering the reactor could be expected to hinder the reaction. In addition, it is unexpected that the catalyst would be stable in the presence of water at reaction conditions. It is therefore quite unexpected that the introduction of water would produce an enhancement in the reaction rate.

The process of the instant invention is illustrated in greater detail by the following examples. It is understood that these examples are not intended to limit the invention in any way. Obvious modifications will occur to those skilled in the art.

EXAMPLE 1—Shows the Activity of a New Catalyst

To a 2 liter autoclave is charged 700 milliliters of a solution containing hydridocarbonyl tris(triphenylphosphine) rodium (I) and an added 16 equivalents of triphenylphosphine in freshly distilled isobutyraldehyde at a rhodium concentration of 55 micrograms per milliliter. Two hundred grams of propylene from a preweighed bomb is then charged, using synthesis gas for pressure, to the autoclave. After heating to 100° C., synthesis gas is charged through a constant pressure regulator to the reactor at 1000 psig. After 15 minutes the synthesis gas is turned off and the reaction is quenched with glycol cooling. On workup, 132 grams of butyraldehyde are obtained.

EXAMPLE 2—Shows the Activity of a Poisoned Catalyst

A catalyst recycle stream sample containing 190 micrograms per milliliter rhodium and 65 percent by-products boiling higher than the butyraldehyde products is withdrawn from a continuous oxo reaction after 11 days of operation. The original catalyst fed to the system was hydridocarbonyl tris(triphenylphosphine) rhodium (I) with an added 16 equivalents of triphenylphosphine in butyraldehydes.

A sample of this used catalyst stream is diluted with freshly distilled isobutyraldehyde to produce a mixture containing 55 micrograms of rhodium per milliliter. 700 Milliliters of this mixture is charged to a 2 liter autoclave. The procedure of Example 1 is repeated using the same synthesis gas mixture. Only 80 grams of butyraldehyde is made in 15 minutes.

EXAMPLE 3—Shows That Gas Stripping Can Restore the Poisoned Catalyst to Its Original Activity A sample of the poisoned catalyst recycle stream containing 190 micrograms per milliliter rhodium described in Example 2 is fed to a gas stripper maintained at 100° C. to 105° C. at 75 milliliters per hour and stripped with 21 moles per hour of nitrogen until the catalyst concentration is 1280 micrograms of rhodium per milliliter. The overhead from the gas stripper contains no rhodium. The stripped catalyst solution is diluted with freshly distilled isobutyraldehyde to a concentration of 55 micrograms of rhodium per milliliter. As in Example 2, 700 milliliters of this solution are charged to a 2 liter autoclave. The procedure of Example 1 is repeated using the same synthesis gas mixture. On workup 133 grams of butyraldehyde is made in 15 minutes.

In a second reaction which was an exact repeat of the above, 132 grams of butyraldehyde is made in 15 minutes.

These results are identical to those obtained with new catalyst (see Example 1).

EXAMPLES 4-6—Show That High Boiler Formation Is Reduced By Water Addition to the Reactor In a typical experiment 1200 milliliters of a 2 to 1 normal to isobutyraldehyde mixture containing hydridocarbonyl tris(triphenylphosphine) rhodium (I) plus 16 equivalents of triphenylphosphine at 50 ppm rhodium weight per volume is charged to a 2 liter autoclave. In Examples 5 and 6, 25 milliliters of water is added. The reactor is charged with 500 psig of synthesis gas (Examples 4 and 5) or nitrogen (Example 6) and heated to 100° C. The pressure of the gas is maintained at 1000 psig. Samples are chromatographed on a daily basis.

At the end of each run a sample is stripped in vacuo to determine the high boiler content. Table I summarizes these results.

TABLE I

| | | | Oxo High Boiler Formation | | | | |
|---|---|---|---|---|---|---|---|
| Example | Temp., °C. | Pressure, psig | Gas | Time, hr. | Catalyst, ppm Rh w/v | High Boilers, % | Remarks |
| 4 | 100 | 1000 | Synthesis Gas | 161 | 50 | 22 | Dry aldehydes |
| 5 | 100 | 1000 | Synthesis Gas | 161 | 50 | 16 | Wet aldehydes |
| 6 | 100 | 1000 | Nitrogen | 161 | 50 | 17 | Wet aldehydes |

These results show that the rate of formation of high boilers at reaction conditions is 0.14 weight percent per hour in dry aldehydes and is reduced to 0.10 weight percent per hour by adding 2.5 weight percent water to the reaction mixture.

EXAMPLE 7—Shows That a Caustic Wash Does Not Restore the Catalyst Actvity of a Poisoned Catalyst A sample of the poisoned catalyst recycle stream containing 190 micrograms per milliliter rhodium, as described in Example 2, is washed with two 500 milliliter portions of 0.1 N caustic solution and then diluted with freshly distilled isobutyraldehyde to give 700 milliliters of solution containing 55 micrograms of rhodium per milliliter. This solution is charged to a 2 liter autoclave and the procedure of Example 1 is repeated using a similar synthesis gas mixture (i.e., 1 to 1 hydrogen to carbon monoxide). On workup, only 76 grams of butyraldehydes are produced during a 15 minute run. Within experimental error this is the same as produced with an untreated poisoned catalyst. Thus a caustic wash does not restore catalyst activity for our system.

EXAMPLE 8—Shows That Butyric Acid Poisons the Catalyst

To the reaction mixture described in Example 1 is added 2 percent isobutyric acid. On repeating the procedure of Example 1 using a similar synthesis gas mixture, 72 grams of aldehydes are produced. This clearly shows that isobutyric acid is one possible poison for the catalyst system.

EXAMPLES 9 and 10—Show That the Reaction Rate in Dry Aldehydes Is Very Close to That Obtained in Aldehyde Saturated With Water These examples use a synthesis gas with a hydrogen to carbon monoxide ratio of 1.07 to 1 which is higher than in previous examples.

EXAMPLE 9

The procedure of Example 1 is repeated using dry isobutyraldehyde. One hundred forty-one grams of butyraldehyde is produced in 15 minutes.

EXAMPLE 10

The procedure of Example 1 is repeated using isobutyraldehyde saturated with water. One hundred forty-six grams of butyraldehyde is produced in 15 minutes.

EXAMPLES 11 and 12—Show That When Water and Aldehydes Are Fed as Two Phases, the Rate is Enhanced Compared to Runs Made in Water Saturated Aldehydes (i.e., Faster Than in Dry Aldehydes)

For the following examples a hydrogen to carbon monoxide ratio of 1.10 to 1 is used.

EXAMPLE 11

The procedure of Example 1 is repeated using isobutyraldehyde saturated with water. One hundred ninety-six grams of butyraldehyde is produced in 15 minutes.

EXAMPLE 12

The procedure of Example 1 is repeated using isobutyraldehyde saturated with water and 1.7 percent additional water to produce a two phase system. Two hundred fifteen grams of butyraldehyde is produced in 15 minutes.

The invention has been described in detail with particular reference to certain preferred embodiments thereof, but it will be understood that variations and modifications can be effected within the spirit and scope of the invention.

I claim:

1. In a process for the hydroformylation of olefins to produce aldehydes which comprises contacting an alpha-olefin having up to about 20 carbon atoms with carbon monoxide and hydrogen in the presence of a catalytic quantity of a complex catalyst consisting essentially of rhodium in combination with carbon monoxide and a triorganophosphorus ligand selected from the group consisting of trialkylphosphines, tricycloalkylphosphines, triarylphosphites and triarylphosphines wherein there is present at least two moles of said ligand per mole of rhodium at a temperature of from about 90° C. to about 160° C. the improvement wherein the reactor feed is a two-phase system consisting of an aqueous phase and an organic phase comprising said alpha-olefin, complex catalyst and ligand and the reaction takes place at a pressure of from about 500 psig to about 3000 psig in the presence of from about 0.1 to about 10% of water.

2. A process according to claim 1 wherein the temperature of the reaction is from about 100° C. to about 140° C.

3. A process of claim 1 wherein the pressure is from about 900 psig to about 1100 psig.

4. A process of claim 1 wherein the pressure is from about 750 psig to about 1500 psig.

5. A process of claim 1 wherein the catalyst is present in the extent of from about 1 part per million to about 1000 parts per million based on the rhodium content of the catalyst.

6. A process of claim 5 wherein the catalyst is present from about 10 to about 100 parts per million.

7. A process according to claim 1 wherein the effluent from the reactor is separated into a product stream and a catalyst containing stream which catalyst containing stream is subsequently regenerated by stripping with a hot gas at a temperature of less than about 160° C.

8. A process according to claim 7 wherein the stripping is accomplished at a temperature of less than about 110° C.

9. A process according to claim 7 wherein the stripping gas is selected from the group consisting of nitrogen, alpha-olefins, synthesis gas or gases recovered from the reactor effluent.

10. A process according to claim 9 wherein the stripped catalyst containing stream is adjusted to the desired rhodium concentration with an aldehyde and recycled to the reactor.

11. A process according to claim 8 wherein the stripping gas is selected from the group consisting of nitrogen, alpha-olefins, synthesis gas or gases recovered from the reactor effluent.

12. A process according to claim 11 wherein the stripped catalyst containing stream is adjusted to the desired rhodium concentration with an aldehyde and recycled to the reactor.

13. A process according to claim 9 wherein the stripping gas is selected from the group consisting of ethylene, propylene, butene-1, and isobutylene.

14. A process according to claim 13 wherein the stripped catalyst containing stream is adjusted to the desired rhodium concentration with an aldehyde and recycled to the reactor.

15. A process according to claim 11 wherein the stripping gas is selected from the group consisting of ethylene, propylene, butene-1, and isobutylene.

16. A process according to claim 15 wherein the stripped catalyst containing stream is adjusted to the desired rhodium concentration with an aldehyde and recycled to the reactor.

* * * * *